US006676601B1

(12) United States Patent
Lacoste et al.

(10) Patent No.: US 6,676,601 B1
(45) Date of Patent: Jan. 13, 2004

(54) APPARATUS AND METHOD FOR LOCATION AND TREATMENT USING ULTRASOUND

(75) Inventors: Francois Lacoste, Rueil Malmaison (FR); Dominique Cathignol, Genas (FR)

(73) Assignees: Technomed Medical Systems, S.A., Vaulx en Velin (FR); Institut National de la Sante et de la Recherche Medicale (Inserm), Paris (FR)

( * ) Notice: Subject to any disclaimer, the term of this patent is extended or adjusted under 35 U.S.C. 154(b) by 0 days.

(21) Appl. No.: 09/744,666
(22) PCT Filed: May 26, 2000
(86) PCT No.: PCT/FR00/01440
§ 371 (c)(1),
(2), (4) Date: Apr. 6, 2001
(87) PCT Pub. No.: WO00/72919
PCT Pub. Date: Dec. 7, 2000

(30) Foreign Application Priority Data

May 26, 1999 (FR) .............................. 99 06627

(51) Int. Cl.[7] .................................................. A61B 8/00
(52) U.S. Cl. ........................ 600/439; 600/453; 600/454; 600/455; 601/2
(58) Field of Search ................................ 600/439, 437, 600/411, 427, 447, 453, 454, 455, 371; 601/2, 3, 4

(56) References Cited

U.S. PATENT DOCUMENTS

| | | | | |
|---|---|---|---|---|
| 5,279,282 A | * | 1/1994 | Oppelt ........................... | 601/4 |
| 5,370,120 A | * | 12/1994 | Oppelt et al. ................. | 600/439 |
| 5,419,327 A | * | 5/1995 | Rohwedder et al. ......... | 600/439 |
| 5,435,304 A | * | 7/1995 | Oppelt et al. ................. | 600/439 |
| 5,624,382 A | * | 4/1997 | Oppelt et al. ................. | 601/2 |
| 5,759,162 A | * | 6/1998 | Oppelt et al. ................. | 601/2 |
| 5,882,302 A | * | 3/1999 | Driscoll, Jr. et al. ......... | 600/371 |

* cited by examiner

Primary Examiner—Sang Y. Paik
Assistant Examiner—Fadi H. Dahbour
(74) Attorney, Agent, or Firm—Welsh & Katz, Ltd.

(57) ABSTRACT

A method for treating myomas or tumors having a pedicle includes the steps of locating the pedicle of a myoma or a tumor using Doppler echography and delivering focused ultrasound to the pedicle.

28 Claims, 2 Drawing Sheets

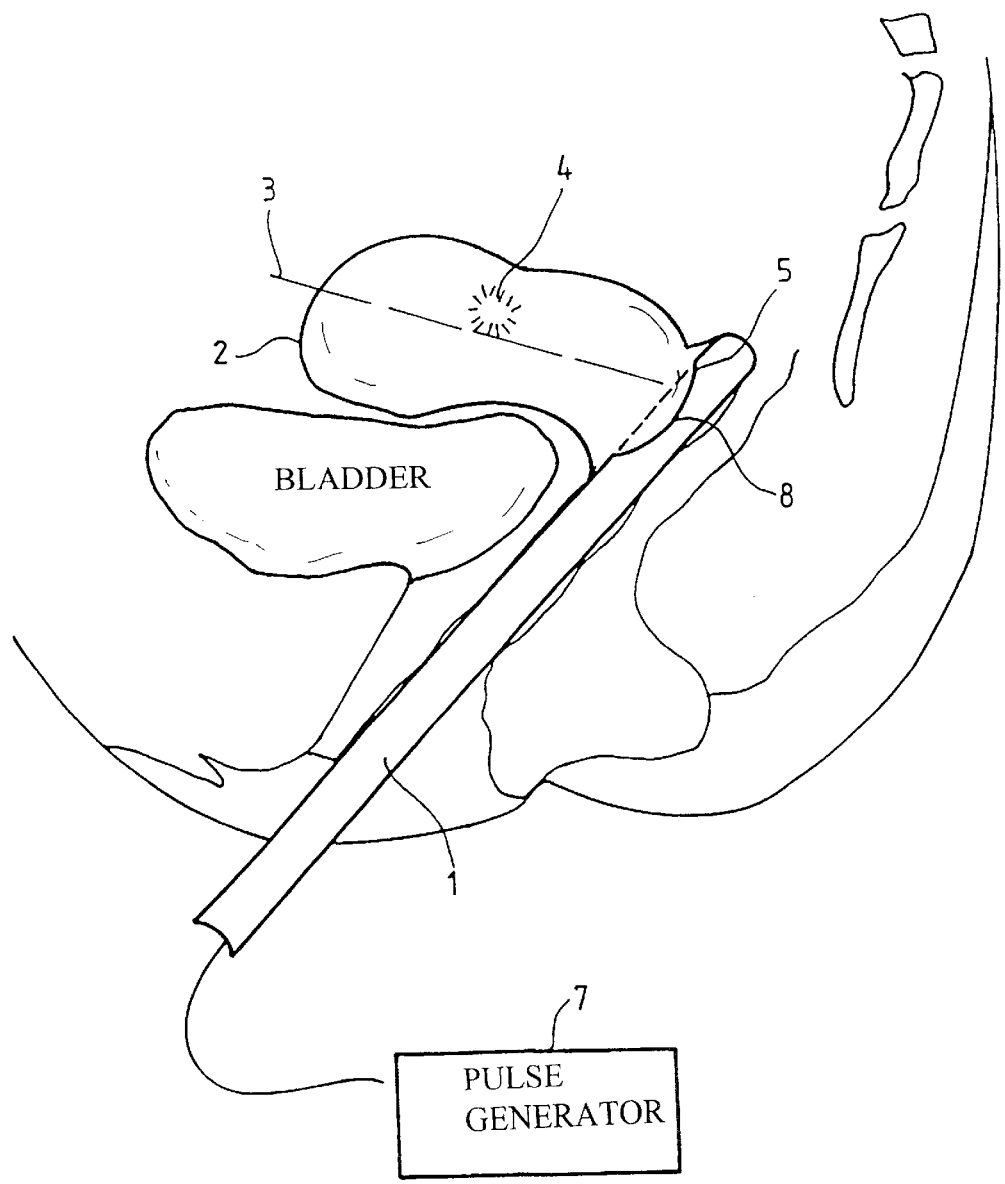

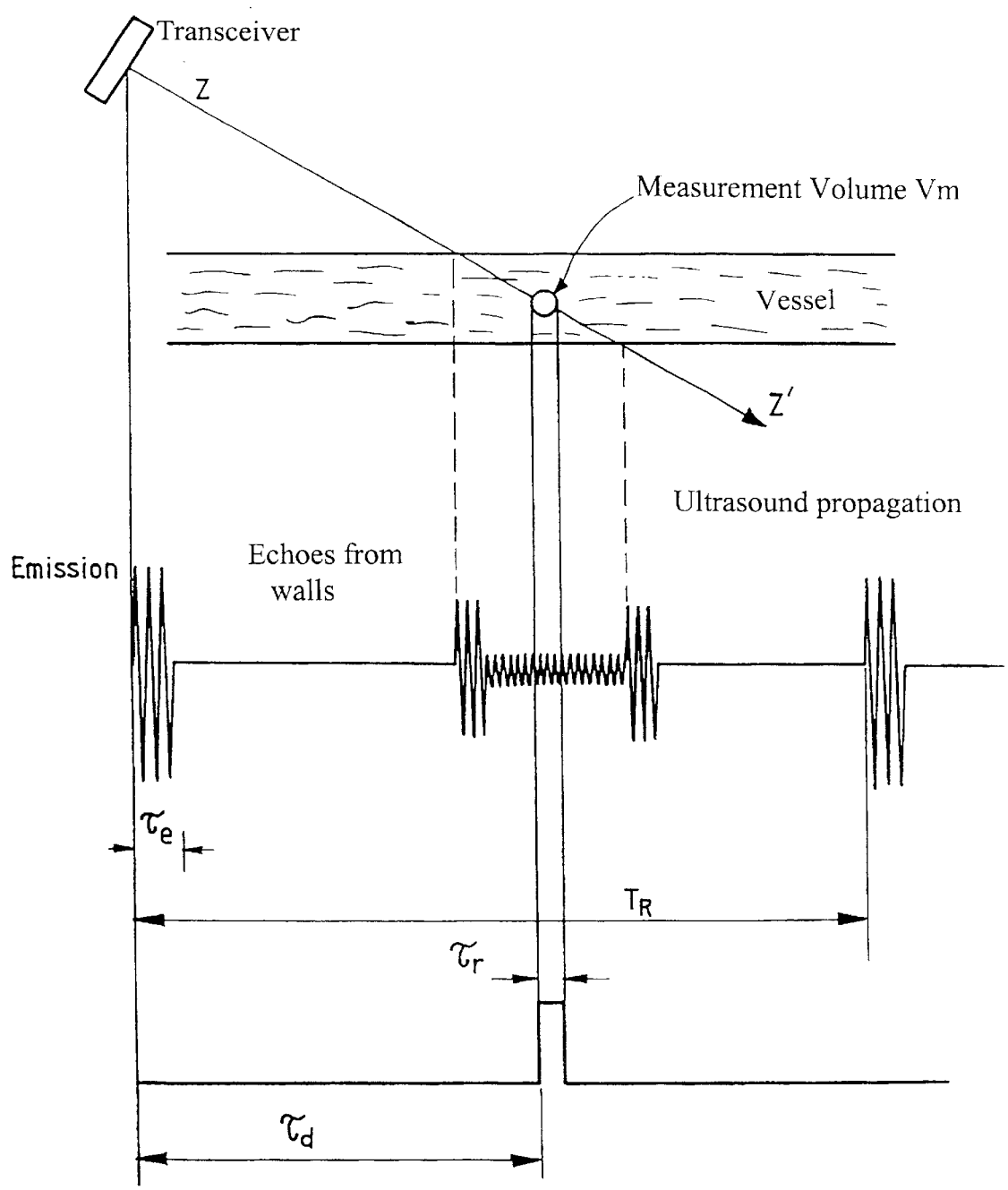
FIG_2

APPARATUS AND METHOD FOR LOCATION AND TREATMENT USING ULTRASOUND

FIELD OF THE INVENTION

The present invention relates to apparatus for location and treatment using ultrasound. It notably applies to focused ultrasound treatment of myomas or other types of tumor having a pedicle. It also applies to the locating and treatment of blood vessels.

BACKGROUND OF THE INVENTION

Myomas are accumulations of muscular tissue attached to the uterus, or, in; other words, are particular fibromas. Three types, depending on their location, are distinguished:

subserous, i.e. external to the uterine cavity;

in the uterine wall, inside the uterine cavity.

Subserous myomas are of little concern, except when they are very large. Myomas in the uterine wall present problems of bleeding. Myomas inside the uterine wall become reduced after the menopause except where the patient receives hormone replacement treatment. They require treatment if they prevent conception.

Myoma ablation involves the use of the following surgical techniques:

myomectomy by laparotomy;

myomectomy by coelioscopy;

hysterotomy by hysteroscopy.

Myomectomy by laparotomy or coelioscopy has the disadvantage of the cicatrix on the uterine wall remaining fragile. Intervention by hysteroscopy presents the problem of limiting operation time due to bleeding and glycocoll resorption. This procedure consequently only applies to small myomas, i.e. from 3 to 4 mm. This procedure further requires great operational skill, and can be dangerous.

It has further been proposed, experimentally, to treat myomas by embolization; the essential problem with this treatment is that it is very painful during expulsion of the necrosed mass.

Myomas are visible by abdominal or transvaginal echography. With transvaginal echography, the probe is placed on the axis of the vagina, perpendicular to the major axis of the uterus. With abdominal echography, the probe is placed on the patient's abdomen.

The technique of hystero-echography is advantageously employed for locating the myoma. A small amount of serum is instilled for separating the two loops of the uterus, typically using a 2 mm catheter introduced by vaginal route. This technique is not painful in view of the very small pressure needed to detach the loops of the uterus.

B-mode echography can be used to identify the fibroma, its anatomical relations and the vascularization around the fibroma which is irrigated at its periphery from a pedicle.

In a quite separate therapeutic area, ultrasound treatment and locating probes have been proposed for benign prostate hyperplasia treatment. One can notably refer to WO-A-89 07909 (Fry), or WO-A-95 02994, in the name of the applicant. These probes are suitable for prostate treatment, but do not have the geometrical and ultrasound characteristics allowing myoma treatment. For ultrasound location, these probes comprise echographic transducers used in A- or B-mode. WO-A-93 17646 discloses ultrasound prostate treatment apparatus; the apparatus has an external therapy transducer. For imaging, it is proposed, firstly, to use a rectal probe and, secondly, to provide an imaging probe at the center of the transducer. Again, there is nothing in this document suggesting treatment of myomas or tumors having a pedicle.

Further, tests have been carried out for attempting to coagulate blood vessels by focused ultrasound: see for example Delon-Martin C., Vogt C., Chignier E., Guers C., Chapelon JY., Cathignol D., "Venous thrombosis generation by means of High Intensity Focused Ultrasound." Ultrasound Med. & Biol.; 21; 113–119; 1995. However, that article does not provide for secondary necrosis of tissue. The authors employ Doppler echography for monitoring blood flow before and after exposure, i.e. for evaluating the effects of ultrasound application. They do however not use Doppler echography for locating the vessels to be treated.

The article by Schultz-Haak "Ultrasonic treatment of varicose veins" in Journal of Vascular Diseases Vol. 40, No. 2, Feb. 129–137 provides for focused ultrasound treatment of certain uterine afflictions but does not disclose the precise apparatus for this. Finally, Moussatov AG, Baker AC, Duck FA envisaged certain gynaecological treatment using focused ultrasound in their article "A possible approach to the treatment of polycystic ovarian syndrome using focused ultrasound" Ultrasonics 36, 893–900 1998. There is no mention of myomas in this article and there is no description of apparatus needed for destroying or locating them.

U.S. Pat. No. 5,880,302 discloses apparatus for hemostatis treatment. This apparatus is designed to stop internal post-traumatic bleeding using focused ultrasound. The apparatus takes the form of a probe designed for introduction into a cavity, such as the vagina, oesophagus, etc; it has a transducer element which is associated with an imaging probe; the latter uses Doppler imaging for producing an image of the region to be treated, and notably of blood flow. Doppler imaging can also be used for providing information about the regions treated. There is nothing in that document suggesting treatment of myomas or tumors by pedicle necrosis. Finally, this document does not indicate how the probe can be positioned using Doppler imaging.

European patent application 0,734,742 discloses therapy apparatus using external ultrasound, consisting of an electronically-focused therapy transducer, with an imaging probe. In one embodiment, the use of two-dimensional Doppler imaging is proposed. This document also does not suggest treatment of myomas or tumors having a pedicle. There is no explanation regarding probe positioning.

There is consequently a need for myoma treatment apparatus, allowing their destruction, which is:

ambulatory (ie without hospitalisation)

preferably, without anaesthetic without blood loss easy to use;

accompanied by a minimum of secondary effects or complications;

and which allows ready and effective location of regions to be treated.

SUMMARY OF THE INVENTION

The invention allows myoma treatment, with all these advantages. It applies more particularly to the treatment of myomas inside the uterine cavity as well as myomas situated in the uterine wall or on the other side thereof with respect to the probe, to the extent they can be reached by the probe of the invention, determined by the focal length of the ultrasound transducer employed.

The invention also provides simplified location and treatment of blood vessels.

More precisely, the invention provides apparatus for location and treatment using ultrasound, comprising at least one therapy transducer and at least one imaging transducer, and a pulse generator exciting said therapy transducer, and exciting said imaging transducer for Doppler echography. It is particularly advantageous for the imaging transducer to be in a fixed position at the center of the therapy transducer.

Doppler echography can be used for locating the region to be treated, for positioning the therapy transducer, before or during therapy; it also can be used to indicate the end of treatment.

In one preferred embodiment, the pulse generator excites the imaging transducer for pulsed Doppler echography.

In one embodiment of the apparatus, the therapy transducer is carried on a probe, preferably a vaginal probe.

In the case of a vaginal probe, the therapy transducer is arranged at an end of the probe, for allowing uterine tissue treatment.

Preferably, the therapy transducer has a focal length suitable for uterine myoma treatment when the probe is introduced into the patient's vagina.

In a further embodiment of the apparatus, the imaging transducer is arranged on said probe.

In this case, the imaging transducer and therapy transducer can be one and the same unit.

In a further embodiment, the apparatus has a second probe, preferably external, on which said imaging transducer is provided.

In the latter case, the apparatus can comprise means for measuring the relative position of the probe carrying said therapy transducer and said probe carrying the imaging transducer.

The invention also provides a method for positioning a therapy transducer in apparatus according to one of claims 1 to 10 for subsequent treatment of a tumor having a pedicle or a myoma, comprising a step of maximizing the Doppler signal from the imaging transducer.

Further characteristics and advantages of the invention will become more clear from the description that follows of some embodiments of the invention, provided by way of example and with reference to the attached drawings.

BRIEF DESCRIPTION OF THE DRAWINGS

FIG. 1 is a diagrammatical view of the probe according to the invention, in the treatment position.

FIG. 2 explains the principle of the Doppler effect flowmeter using pulsed ultrasound emission.

DESCRIPTION OF THE INVENTION

The invention is described below in its application to myoma treatment; the apparatus consequently comprises a probe giving access to myomas by vaginal route. The invention is however not limited to this type of apparatus, and could be used for external treatment, in which case the therapy transducers are not necessarily carried by a probe, but can be arranged on a sphere, or on a carrier for providing geometrical or electronic focusing.

In the embodiment described, the invention proposes using, for myoma treatment, focused ultrasound delivered by a vaginal probe. Additionally, the invention proposes using Doppler echography for locating the region to be treated. In this way, apparatus according to the invention allows myoma treatment, by vaginal route, using for example the following operating modes:
- sweeping the myoma with the focused spot of the therapy probe, in order to provoke necrosis of or coagulate the mass of the myoma;
- sweeping the myoma pedicle with the focused spot of the therapy probe in order to provoke necrosis or coagulate the blood vessels composing it; in this case, tissue mass necrosis proceeds by ischemia.

Following ultrasound myoma treatment according to the invention, small myomas are expulsed spontaneously. In other cases, it may be necessary to remove the myoma mass. As this is coagulated tissue, the operation is facilitated: no bleeding is caused and the amount of matter to be removed is reduced; because of this, one can envisage, even for large myomas, intervention by hysteroscopy.

The invention also uses Doppler echography for myoma location before and during treatment, and preferably echography in pulsed Doppler mode, described with reference to FIG. 2. This ensures simple and accurate myoma location.

FIG. 1 is a diagrammatical view of the probe according to the invention, in the position for treating a myoma. As shown in FIG. 1, probe 1 is a vaginal probe, introduced into the patient's vagina with the end of the probe close to the neck of the uterus 2. The longitudinal axis of the probe in the treatment position shown in FIG. 1 is substantially perpendicular to the major axis of the uterus, shown in FIG. 1 by dashed line 3. Reference numeral 4 is a myoma to be treated, on the uterine wall.

As FIG. 1 shows, the probe has, close to its end, a treatment transducer or therapy transducer 5, which emits ultrasound in a direction substantially perpendicular to the longitudinal axis of the probe. This transducer can be fixed or movable in the probe body, notably depending on the location mode chosen, and on the necessity of allowing the passage of an imaging transducer. For this, one can use the teachings of International Application WO-A-95 02 994 for mounting the transducer in the probe, or, yet again, a guard ring as taught in French patent 2,750,340. It is advantageous for the transducer to be moveable inside the probe so as to allow the region to be treated to be swept without the probe itself moving. This solution avoids movement of the region to be treated brought about by probe movement, resulting from sweeping. The transducer could also be mounted non-perpendicular, and for example at about 45° to the axis, in a configuration similar to that used in imaging transducers in so-called vaginal ultrasound scanning probes.

One can additionally, if necessary, hold the probe in position during treatment using an intra-uterine anchoring device. Such a device is known per se. The device is advantageously stationary at the end of the probe for avoiding all movement thereof once it is in the treatment position.

The therapy transducer can have a shape that provides geometrical ultrasound focusing, as shown in FIG. 1; electronic focusing can also be provided, with a plane or non-spherical transducer. The term therapy transducer covers not only a transducer formed from a single ceramic element of suitable geometrical shape adapted for ultrasound focusing, but also a transducer formed from a set of ceramic elements that are excited independently of each other allowing electronic focusing.

The probe is connected to a pulse generator 7 providing excitation of the therapy transducer. The generator supplies the ceramic element or elements constituting the transducer with electric pulses of adjustable length and intensity, for applying, via the therapy transducer, therapy ultrasound. By therapy ultrasound we mean ultrasound having a deliberate destructive or tissue necrosing effect, by heat or by the cavitation effect. Such therapy ultrasound typically has an energy density greater than 1000 W/cm$^2$.

In a first embodiment, the apparatus also has an imaging transducer, and a pulse generator for exciting this transducer for locating the region to be treated and guiding the firing. The pulse generator for the imaging transducer and for the therapy transducer do not supply pulses of the same power; they can nevertheless be grouped together into a single housing, and will be simply referred to below as the "pulse generator". Preferably, as explained with reference to FIG. 2, the imaging transducer operates by pulsed Doppler echography, and supplies not only an indication of direction, but also of distance. The imaging transducer can be a single one-piece transducer, or may comprise several elements or ceramic elements, like the therapy transducer.

The imaging transducer can be integrated into the transvaginal probe using an arrangement similar to that employed in prior art apparatus discussed above. Thus, it is advantageous for the imaging transducer to be able to visualize the treatment region, with or without relative movement of the imaging transducer with respect to the therapy transducer. For example, the imaging transducer can be fixed at the center of the therapy transducer, as shown by reference numeral 8 in FIG. 1. Arrangements can be made for the therapy transducer to move away to allow the imaging transducer to move to a locating position. One can also arrange for the imaging transducer to move into position for imaging, and then withdraw it for therapy. If the imaging transducer and therapy transducer are in a fixed relationship one to the other, it is advantageous for them to have the same focal length.

In a second embodiment of the apparatus, the imaging transducer can be independent of the therapy probe, the imaging transducer being, for example, comprised in a conventional ultrasound probe. In the case of myomas, myoma location can be performed by trans-abdominal echography, over a distance of 7 to 8 cm after passing through the bladder. Relative movement of the imaging probe and therapy probe can be coordinated to allow the focal point of the therapy transducer to be brought to the desired position. One solution for coordinating movement consists in mounting the probes on carriers the movement of which is able to be measured, for example an articulated arm the movements of which are encoded, as in European patent application 0,247,916; in this case, one can proceed with introducing the therapy probe, then with acquiring the relative position of the two probes for example by aiming a given point on the therapy probe at the image supplied by the imaging probe. Following this acquisition, it is sufficient to track therapy probe and imaging probe movements to know their position.

For coordinating therapy probe and imaging probe movements, one could also use a remote encoding system which is known per se, such as remote encoding systems using infra-red, magnetic or ultrasound transmission.

In this third embodiment, a single transducer is used for treatment and for locating blood vessels in pulsed Doppler mode. These vessels can for example be part of the myoma pedicle. In one alternative embodiment, only a part of the transducer can be used for location. The advantage of this configuration is the space saving resulting from the absence of a supplementary imaging transducer. The apparatus can be simplified as now there is no mechanical sweep involved. When treating blood vessels this is indeed unnecessary as their diameter is generally of the same order of magnitude as the focal region of the treatment transducer. Firing to the same place can be done.

The embodiments just mentioned can be combined. Thus, the external probe could be used for prior locating using echographic imaging, advantageously using color Doppler mode if the practitioner wishes to treat blood vessels, or the pedicle of a myoma; the vaginal probe is then introduced and manipulated by the operator so that the focal point of the transducer coincides with the pedicle. This positioning can be performed thanks to the imaging transducer provided on the probe, which enables the pedicle of the myoma, or the pedicle itself to be viewed; in effect, echography in pulsed Doppler mode is directive and allows distance measurement, as explained with reference to FIG. 2. One can also, in the first or second embodiment, use a therapy probe with no provisions for sweep.

The apparatus of the first embodiment of the invention operates as follows. The operator introduces the probe into the patient's vagina-using the imaging transducer for visualising the region to be treated, and for positioning the probe so as to bring the focal point of the therapy transducer into the region of the area to be treated. It is clearly advantageous, in this; case, to use an imaging transducer operating with Doppler echography, to also allow distance measurement. If necessary, the imaging probe is moved out of the way, and therapy treatment then starts. The treated region can be visualized between two treatment steps to check the effects of treatment.

In the case of the second embodiment, the apparatus operates as follows. The operator inserts the therapy probe into the patient's vagina so that the therapy transducer is substantially in the firing position. In this position, the transducer can be 2 or 3 centimetres from the region to be treated.

The operator then proceeds to locate the region to be treated, for example using B-mode echography or pulsed mode Doppler echography, as described above. The operator sets the relative position of the imaging transducer and the probe, as explained above.

After it has been located, the region to be treated is delimited and treatment can start.

In both embodiments, for treatment, the therapy transducer delivers power ultrasound towards the region to be treated, optionally sweeping the region. The effect of the ultrasound is to raise the region to be treated to a high temperature, typically a temperature above 45° C., in as short a time as possible.

Treatment can be done for myomas by coagulating their mass, for example by progressively sweeping the therapy transducer focal spot over the region to be treated. One can also coagulate the pedicle in other words the blood vessels composing it and which supply the fibroma. In this case, the tissue mass will undergo necrosis by ischemia. This pedicle blood vessel coagulation can be obtained as indicated in the article by Delon-Martin C. et al., referenced above. Other pedicle treatment protocols can also be used. Vessel coagulation can be direct, by heating the vessels and blood contained therein. In this case, ultrasound intensity is relatively modest, for example of the order of 1000 W/cm$^2$. Vessel coagulation can also be indirect, ultrasound being delivered with a high intensity, typically above 10,000 W/cm$^2$, so as to damage vessel walls, thereby provoking embolism. This treatment procedure applies not only to myomas, but also to other types of tumor having a pedicle or which are supplied by localized blood vessels.

The third embodiment of the invention is particularly advantageous for destroying blood vessels, for example those contained in the pedicles forming the basis of certain tumors, for example vesical or rectal polyps, or certain uterine myomas. In this framework, the practitioner would proceed as follows: after introducing the probe close to the vessel to be destroyed, the probe is set to pulsed Doppler transmission-reception mode and the signal is observed. The probe is moved facing the vessel so as to maximise the Doppler signal, which indicates that the vessel is on the transducer axis. Then, while observing the distance between the transducer and echogenous source (the vessel) the probe is moved along the transducer axis so that the focal point of the transducer is located on the vessel. Firing can now be performed.

In all cases, between each shot, in other words, between each delivery of an ultrasound train, the imaging transducer can be used for checking the effect of ultrasound application, and above all for guiding the shots; it is advantageous to carry out checking, between each shot, of the position of the region to be treated. For this purpose, automatic tracking of the region to be treated by the therapy transducer can be provided, based on information supplied by the imaging transducer. The region to be treated could also be displayed, on a screen, showing the treated region; the operator can also be given the possibility of halting treatment if the treated region has shifted with respect to the therapy transducer focal spot.

The invention also allows treatment of myomas, blood vessels or other types of tumor or similar having a pedicle, following a simple and risk-free protocol. Risks of burning are limited; unlikely burns at the interface between the probe and tissue would be without consequence.

FIG. 2 is a diagram explaining the principle of the pulsed emission Doppler effect flowmeter. This figure shows the transducer acting as a transceiver, a blood vessel of measurement volume Vm and, at the bottom of FIG. 2, the ultrasound transmitted and received by the transducer.

Generally speaking, Doppler effect apparatus allows detection of blood flow facing the ultrasound probe. A distinction is habitually made between continuous emission Doppler flowmeters and pulsed emission Doppler flowmeters. The first of these indicate whether, facing the probe, there is or there is not blood flow but do not indicate at what depth blood flow is occurring. The second type make it possible to determine not only the existence of blood flow, but also the distance of blood flow with respect to the probe.

As FIG. 2 shows, the transducer periodically sends an ultrasound wave train of a duration $\tau_e$; this duration is typically of the order of several periods, for example some 10 periods. Ultrasound is emitted at a frequency of 1 to 20 MHz depending on the depth of exploration. The greater the depth, the lower the frequency. In the case of myoma treatment according to the invention, a frequency of 3 to 5 MHz is suitable.

The ultrasound is reflected by the various interfaces situated in the direction of ultrasound propagation, and notably by vessel walls. The sound is also reflected by moving particles, with a different frequency, due to the particle movement; the frequency difference is called the Doppler effect and allows particle velocity to be determined. The reflected ultrasound is received by the same transducer which now plays the role of a receiving transducer.

The time difference between sending and receiving the various echoes is a function of the distance between the transducer and the target that caused reflection. Studying the received signal makes it possible to determine velocity in a determined volume and to obtain, point by point, the speed of targets located along the zz' ultrasound propagation axis.

In the example of FIG. 2, wall echoes are shown together with echoes originating from moving targets (here, essentially, red blood cells). Ultrasound reflected for example by the particles situated inside measurement volume Vm are received at the receiver after duration $\tau_d$. The size of the volume to be explored is defined by the period $\tau_r$ during which the reflected signals are analysed. In this way, adjusting duration $\tau_d$ makes it possible to determine distance from the target, while adjustment of duration $\tau_r$ makes it possible to determine target volume.

When all are targets to be analysed have been explored, a further wave train is sent. Bearing in mind the distance-frequency ambiguity, the repetition period is of the order of a few kHz up to 20 kHz. In FIG. 2, $\tau_e$ is the duration of a pulse train and $\tau_R$ is the duration between two pulse trains.

For use according to the invention, signal analysis makes it possible to locate the walls of the myoma or of the myoma pedicle. Now, the duration $\tau_d$ and duration $\tau_r$ can be adjusted for measuring blood velocity in the pedicle. Thus, tissue to be treated is located simply and effectively and the focal spot of the therapy transducer can be brought to the region to be destroyed. Similarly, the imaging transducer makes it possible to check for the existence of blood flow after treatment. In effect, when coagulation is complete, the Doppler signal is non-existent.

Doppler effect apparatus of the pulsed type and apparatus developed from these, i.e. duplex systems and color Doppler imagers are described in "*Vélocimétrie Doppler Application en pharmacologie cardio-vasculaire animale et clinique*" by Peronneau, Editions INSERM.

The treatment performed thanks to the invention can consequently comprise the following steps:
  placement or rough positioning of the therapy transducer, for example introduction of an intra-cavital probe into a cavity of the patient;
  location of the region to be treated using Doppler echography, and notably pulsed Doppler echography;
  positioning the therapy transducer for treatment;
  treatment with focused ultrasound with or without sweep.

In an application to treatment of myomas or tumors having a pedicle, therapy transducer positioning can be done by maximising the received Doppler signal. In this way, the therapy transducer focal point can be accurately moved onto the myoma or tumor pedicle.

As explained above, Doppler echography is carried out using either an additional imaging transducer or using the therapy transducer itself, which, in this case, constitutes an imaging transducer. In the first case, the imaging transducer can be on the same carrier as the therapy transducer, or on a separate carrier.

Additionally, between two treatments steps, vizualisation steps by imaging can be provided; this is particularly useful in the treatment of blood flows: blood vessels, myoma pedicles, and the like. Indeed, in this case, disappearance or reduction of the Doppler signal to below a certain threshold can be employed for controlling stopping of treatment.

In the case of a therapy transducer and an imaging transducer on different carriers, it is preferable to provide a step for measurement or calculation of the relative position of the transducers.

Obviously, the invention is not limited to the examples and embodiments described and illustrated, but may be subject to numerous variations accessible to those skilled in the art. The treatment protocol of the invention can comprise alternating location and treatment cycles; provision can also be made for treatment parameter adjustment, as described in applicant's French patent application of May 13, 1998, serial number 98.06044, and entitled "Method for measuring the effect of treatment on tissue".

In particular, the device of the invention can be advantageously employed for coagulating blood vessels using focused ultrasound.

The invention also applies to all types of tumor which are nourished by a pedicle, for example vesical or digestive polyps. Like the case for myomas, the invention allows simple and effective location by Doppler signal measurement, the latter having a maximum when close to the blood vessels supplying the tumor. The invention also allows effective treatment of the tumor, by necrosis of the vessels that feed it. The Doppler signal can also be employed for controling stopping of treatment, when blood flow in the pedicle has reached a threshold value. This threshold can be predetermined or can depend on the initial blood circulation in the pedicle.

In its simplest and most advantageous embodiment, the invention consists of a therapy transducer, an imaging transducer at the center of the therapy transducer which is fixed with respect to the latter; the imaging transducer is connected to a pulse generator exciting it in Doppler mode.

It is also possible to provide separate devices for exciting the therapy transducer and the imaging transducer. The term "pulse generator" covers all the devices able to excite the two transducers.

While the invention has been described for the case of intra-cavital probes, it also applies to external treatment.

What is claimed is:

1. An apparatus for location and treatment using ultrasound comprising:
   at least one therapy transducer;
   at least one locating transducer,
   a pulse generator exciting said therapy transducer, and exciting said locating transducer for Doppler echogaphy; and
   wherein the locating transducer is in a fixed position at the center of the therapy transducer.

2. The apparatus according to claim 1, wherein the pulse generator excites the locating transducer for pulsed Doppler echography.

3. The apparatus according to claim 1, wherein the therapy transducer is carried on a probe, preferably a vaginal probe.

4. The apparatus according to claim 3, wherein the therapy transducer is arranged at an end of the probe, for allowing uterine tissue treatment.

5. The apparatus according to claim 4, wherein the therapy transducer has a focal length suitable for uterine myoma treatment when the probe is introduced into the patient's vagina.

6. The apparatus according to claim 3, wherein the therapy transducer has a focal length suitable for uterine myoma treatment when the probe is introduced into the patient's vagina.

7. The apparatus according to claim 1, wherein the locating transducer and therapy transducer are one and the same unit.

8. The apparatus according to claim 7, wherein a portion of the unit is used for locating.

9. The apparatus according to claim 1, further including a first external probe on which said locating transducer is provided.

10. The apparatus according to claim 9, further including a second external probe in which said therapy transducer is provided, and wherein the apparatus comprises means for measuring a relative position of the second probe carrying said therapy transducer and said first probe carrying the locating transducer.

11. An apparatus for location and treatment using ultrasound, comprising:
    at least one therapy transducer;
    at least one imaging transducer in a fixed position at the center of the therapy transducer;
    a pulse generator exciting the therapy transducer;
    the imaging transducer being excited for Doppler echography; and
    the apparatus adapted to treat a tumor having a pedicle or a myoma, further comprising maximising a Doppler signal from the imaging transducer.

12. A method for treating myomas or tumors having a pedicle, comprising the steps of:
    locating the pedicle of a myoma or a tumor using Doppler echography; and
    delivering focused ultrasound to the pedicle.

13. The method of claim 12, wherein the step of locating comprises using pulsed Doppler echography.

14. The method of claim 12, wherein the step of delivering comprised sweeping the myoma pedicle with a spot of the focused ultrasound in order to provoke necrosis or coagulate the blood vessels composing said pedicle.

15. The method of claim 12, wherein said focused ultrasound has an energy density greater than 1000 W/cm$^2$.

16. The method of claim 12, wherein the step of delivering comprises raising said pedicle to a temperature above 45° C.

17. A method for treating myomas or tumors having a pedicle, comprising the steps of:
    locating a myoma or a tumor using Doppler echography for finding a pedicle of said myoma or tumor; and
    delivering focused ultrasound to the myoma or tumor.

18. The method of claim 17, wherein the step of locating comprises using pulsed Doppler echography.

19. The method of claim 17, wherein the step of delivering comprised sweeping the myoma or tumor with a spot of the focused ultrasound, in order to provoke necrosis of or coagulate the mass of the myoma or tumor.

20. The method of claim 17, wherein said focused ultrasound has an energy density greater than 1000 W/cm$^2$.

21. The method of claim 17, wherein the step of delivering comprises raising said myoma or tumor to a temperature above 45° C.

22. A method for destroying blood vessels, comprising the steps of:
    locating a vessel using Doppler echography; and
    delivering focused ultrasound to the vessel.

23. The method of claim 22, wherein the step of locating comprises using pulsed Doppler echography.

24. The method of claim 22, wherein the step of delivering comprised sweeping the blood vessel with a spot of the focused ultrasound, in order to provoke necrosis of or coagulate the mass of the myoma or tumor.

25. The method of claim 22, wherein said focused ultrasound has an energy density greater than 1000 W/cm$^2$.

26. The method of claim 22, wherein the step of delivering comprises raising said myoma or tumor to a temperature above 45° C.

27. An apparatus for location and treatment using ultrasound, comprising:
    a therapy transducer and a probe configured to carry the therapy transducer;
    an imaging transducer and a probe configured to carry the imaging transducer;

a pulse generator exciting said therapy transducer and exciting said imaging transducer for Doppler echography; and means for measuring the relative position of the probes.

28. An apparatus for location and treatment using ultrasound, comprising: at least one therapy transducer;

at least one imaging transducer in a fixed position at the center of the therapy transducer;

a pulse generator exciting the therapy transducer;

the imaging transducer being excited for Doppler echography and maximizing a Doppler signal from the imaging transducer; and the apparatus adapted to destroy blood vessels.

* * * * *